(12) United States Patent
Oki et al.

(10) Patent No.: US 10,557,626 B2
(45) Date of Patent: Feb. 11, 2020

(54) LIGHT SOURCE APPARATUS AND TEMPERATURE CONTROL METHOD

(71) Applicant: SONY CORPORATION, Tokyo (JP)

(72) Inventors: Tomoyuki Oki, Kanagawa (JP); Hirotaka Muramatsu, Kanagawa (JP)

(73) Assignee: SONY CORPORATION, Tokyo (JP)

( * ) Notice: Subject to any disclaimer, the term of this patent is extended or adjusted under 35 U.S.C. 154(b) by 0 days.

(21) Appl. No.: 16/268,079

(22) Filed: Feb. 5, 2019

(65) Prior Publication Data

US 2019/0170339 A1 Jun. 6, 2019

Related U.S. Application Data

(63) Continuation of application No. 15/559,969, filed as application No. PCT/JP2016/001217 on Mar. 7, 2016, now Pat. No. 10,222,044.

(30) Foreign Application Priority Data

Mar. 31, 2015 (JP) .................. 2015-071745

(51) Int. Cl.
  *H05B 37/02* (2006.01)
  *A61B 1/06* (2006.01)
  *F21V 29/54* (2015.01)
  *G02B 23/24* (2006.01)
  *G02B 21/06* (2006.01)

(52) U.S. Cl.
  CPC ............... *F21V 29/54* (2015.01); *A61B 1/06* (2013.01); *A61B 1/0661* (2013.01); *G02B 23/2469* (2013.01); *G02B 21/06* (2013.01)

(58) Field of Classification Search
  CPC ......... F21V 29/54; A61B 1/06; A61B 1/0661; H05B 37/02; H05B 33/08; G02B 21/06; G02B 23/2469
  See application file for complete search history.

(56) References Cited

U.S. PATENT DOCUMENTS

| 2008/0058602 | A1* | 3/2008 | Landry ............... A61B 1/00055 600/180 |
| 2009/0079360 | A1* | 3/2009 | Shteynberg ......... H05B 33/0818 315/291 |
| 2012/0286666 | A1 | 11/2012 | Shteynberg et al. |

FOREIGN PATENT DOCUMENTS

| CN | 105307555 A | 2/2016 |
| JP | 07-142801 A | 6/1995 |
| JP | 2001-070227 A | 3/2001 |
| JP | 2003-034167 A | 2/2003 |
| JP | 2004-356449 A | 12/2004 |

(Continued)

OTHER PUBLICATIONS

Notice of Allowance and Fees Due for U.S. Appl. No. 15/559,969, dated Oct. 23, 2018, 07 pages.

(Continued)

*Primary Examiner* — Jimmy T Vu

(74) *Attorney, Agent, or Firm* — Chip Law Group

(57) ABSTRACT

A light source apparatus according to an embodiment of the present technology includes a plurality of light source portions, a plurality of temperature adjustment units, and a drive control unit. The plurality of temperature adjustment units are capable of respectively adjusting temperatures of the plurality of light source portions. The drive control unit is capable of controlling a drive timing of each of the plurality of temperature adjustment units.

13 Claims, 9 Drawing Sheets

(56) References Cited

FOREIGN PATENT DOCUMENTS

| JP | 2006-054316 A | 2/2006 |
| JP | 2010-258433 A | 11/2010 |
| JP | 2011-199004 A | 10/2011 |
| JP | 2015-018640 A | 1/2015 |
| WO | 2015/005167 A1 | 1/2015 |

OTHER PUBLICATIONS

Non-Final Rejection for U.S. Appl. No. 15/559,969, dated Jun. 21, 2018, 05 pages.

International Search Report and Written Opinion of PCT Application No. PCT/JP2016/001217, dated May 31, 2016, 08 pages of English Translation and 08 pages of ISRWO.

International Preliminary Report on Patentability of PCT Application No. PCT/JP2016/001217, dated Oct. 12, 2017, 08 pages of English Translation and 06 pages of IPRP.

Office Action for JP Patent Application No. 2017-509299, dated Jul. 16, 2019, 06 pages of Office Action and 05 pages of English Translation.

Office Action for JP Patent Application No. 2017-509299, dated Sep. 17, 2019, 03 pages of Office Action and 03 pages of English Translation.

\* cited by examiner

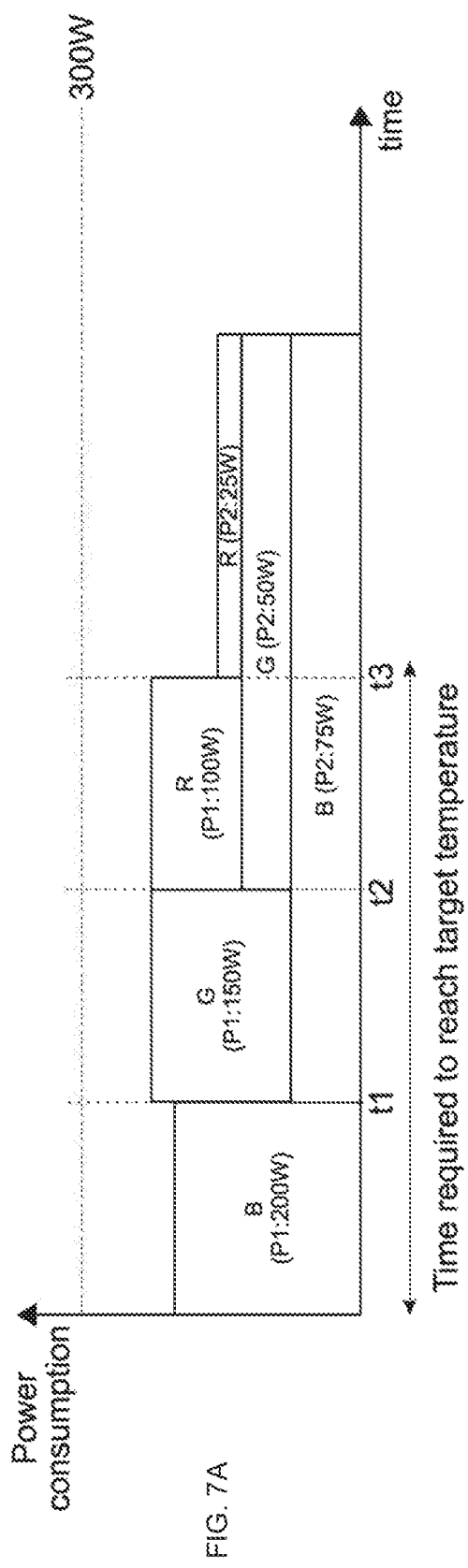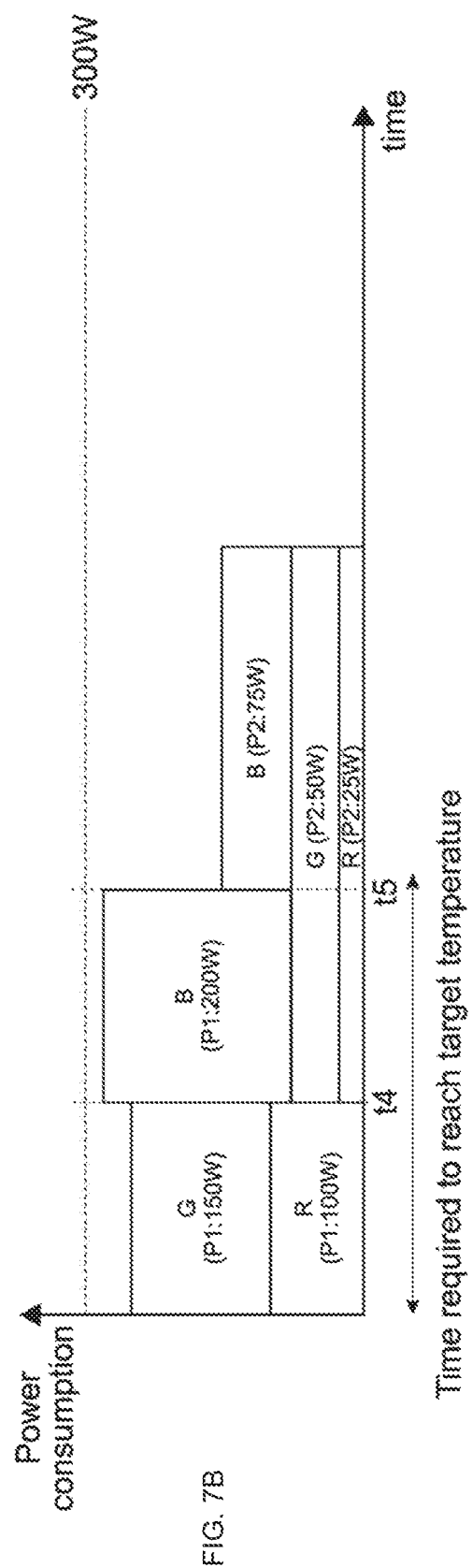

LIGHT SOURCE APPARATUS AND TEMPERATURE CONTROL METHOD

CROSS REFERENCE TO RELATED APPLICATIONS

This application is a continuation application of U.S. patent application Ser. No. 15/559,969, filed Sep. 20, 2017, which is a U.S. National Stage Entry of International Patent Application No. PCT/JP2016/001217 filed on Mar. 7, 2016, which claims priority benefit of Japanese Patent Application No. JP 2015-071745 filed in the Japan Patent Office on Mar. 31, 2015. Each of the above-referenced applications is hereby incorporated herein by reference in its entirety.

TECHNICAL FIELD

The present technology relates to a light source apparatus and a temperature control method applicable thereto.

BACKGROUND ART

In a medical field, there is known a technology of carrying out inspections, diagnoses, and the like by irradiating excitation light onto a living body and measuring fluorescence generated by the excitation. Patent Literature 1 discloses a fluorescent observing device that uses a semiconductor laser as a light source for excitation light. In this fluorescent observing device, excitation light emitted from the semiconductor laser is irradiated onto a body tissue from a tip end portion of an endoscope. Then, fluorescence generated from the body tissue by the excitation light is photographed by an imaging element and displayed on a display unit.

As shown in FIG. 1 of Patent Literature 1, in the semiconductor laser, a Peltier device and a thermistor are arranged so as to be in close contact with each other. By the Peltier device being driven on the basis of a temperature detected by the thermistor, the temperature of the semiconductor laser is constantly kept at 20° C. or less. By adjusting the temperature of the semiconductor laser in this way, an output of excitation light is increased, and a lifetime is prolonged (paragraphs . . . etc. in specification of Patent Literature 1).

CITATION LIST

Patent Literature

Patent Literature 1: Japanese Patent Application Laid-open No. 2001-70227

DISCLOSURE OF INVENTION

Technical Problem

In a case where a temperature of a light source is adjusted using a Peltier device and the like as in Patent Literature 1, power for driving the Peltier device and the like becomes necessary, and thus power consumption increases. In the medical field and the like, the increase of power consumption leads to an increase of a leakage current and may thus inhibit battery drive of an apparatus during an emergency medical care.

In view of the circumstance as described above, the present technology aims at providing a light source apparatus capable of reducing power consumption at a time of adjusting a temperature of a light source portion, and a temperature control method.

Solution to Problem

For attaining the object described above, a light source apparatus according to an embodiment of the present technology includes a plurality of light source portions, a plurality of temperature adjustment units, and a drive control unit.

The plurality of temperature adjustment units are capable of respectively adjusting temperatures of the plurality of light source portions.

The drive control unit is capable of controlling a drive timing of each of the plurality of temperature adjustment units.

In this light source apparatus, the drive timing of each of the plurality of temperature adjustment units capable of respectively adjusting the temperatures of the light source portions is controlled. Accordingly, power consumption in adjusting the temperatures of the light source portions can be reduced.

The drive control unit may drive the plurality of temperature adjustment units such that the respective drive timings differ from one another.

Accordingly, power consumption in the temperature adjustment can be reduced.

The drive control unit may sequentially drive the plurality of temperature adjustment units at predetermined time intervals.

Accordingly, a reduction in power consumption can be realized by simple processing.

The light source apparatus may further include a temperature detection unit capable of detecting a temperature of each of the plurality of light source portions. In this case, the drive control unit may control each of the drive timings on the basis of the temperature detected by the temperature detection unit.

Accordingly, it becomes possible to shorten a time required for the temperature adjustment while reducing power consumption in the temperature adjustment.

The drive control unit may drive a first temperature adjustment unit that adjusts a temperature of a first light source portion and drive, in a case where the temperature of the first light source portion falls within a predetermined range, a second temperature adjustment unit that adjusts a temperature of a second light source portion different from the first light source portion.

Accordingly, the temperature adjustment can be executed efficiently while reducing power consumption in the temperature adjustment.

The light source apparatus may further include a power detection unit capable of detecting power consumption of each of the plurality of temperature adjustment units. In this case, the drive control unit may control each of the drive timings on the basis of the power consumption detected by the power detection unit.

Accordingly, it becomes possible to shorten a time required for the temperature adjustment while reducing power consumption in the temperature adjustment.

The drive control unit may drive a first temperature adjustment unit and drive, in a case where power consumption of the first temperature adjustment unit becomes smaller than a predetermined threshold value, a second temperature adjustment unit different from the first temperature adjustment unit.

Accordingly, the temperature adjustment can be executed efficiently with low power consumption.

The drive control unit may preferentially drive the temperature adjustment unit having lower expense power out of the temperature adjustment units that have adjusted the temperatures of the light source portions and been put to a stationary state.

Accordingly, it becomes possible to shorten a time required for the temperature adjustment.

The drive control unit may be capable of PID (Proportional Integral Derivative)-controlling each of the plurality of temperature adjustment units on the basis of the temperature detected by the temperature detection unit.

By the PID control, temperatures can be adjusted with high accuracy.

The drive control unit may control the respective drive timings such that the drive timings become equal to one another and set PID parameters to be used for the PID control of each of the plurality of temperature adjustment units such that the PID parameters differ from one another.

Accordingly, power consumption in the temperature adjustment can be reduced.

The drive control unit may set one or more provisional target temperatures within a range between a current temperature of the light source portion and a target temperature and execute stepwise the PID control that sets each of the one or more provisional target temperatures and the target temperature as a target value.

Accordingly, power consumption in the temperature adjustment can be reduced.

The drive control unit may control each of the drive timings on the basis of maximum power consumable in adjusting the temperature of each of the plurality of light source portions.

Accordingly, it becomes possible to shorten a time required for the temperature adjustment.

The drive control unit may control each of the drive timings such that a difference between the maximum power and a sum of power consumption detected by the power detection unit falls within a predetermined range.

Accordingly, it becomes possible to shorten a time required for the temperature adjustment.

A temperature control method according to an embodiment of the present technology includes arranging a plurality of temperature adjustment units capable of respectively adjusting temperatures of a plurality of light source portions. A drive timing of each of the plurality of temperature adjustment units is adjusted.

In this temperature control method, the drive timing of each of the plurality of temperature adjustment units capable of respectively adjusting the temperatures of the light source portions is controlled. Accordingly, power consumption in adjusting the temperatures of the light source portions can be reduced.

Advantageous Effects of Invention

As described above, power consumption in adjusting the temperatures of the light source portions can be reduced. It should be noted that the effects described herein are not necessarily limited, and any effect described in the present disclosure may be obtained.

BRIEF DESCRIPTION OF DRAWINGS

FIGS. 7A and 7B Diagrams for explaining an example of setting a priority order for driving the temperature adjustment circuits.

MODES FOR CARRYING OUT THE INVENTION

Hereinafter, embodiments of the present technology will be described with reference to the drawings.

Endoscope Apparatus

Figure 1:
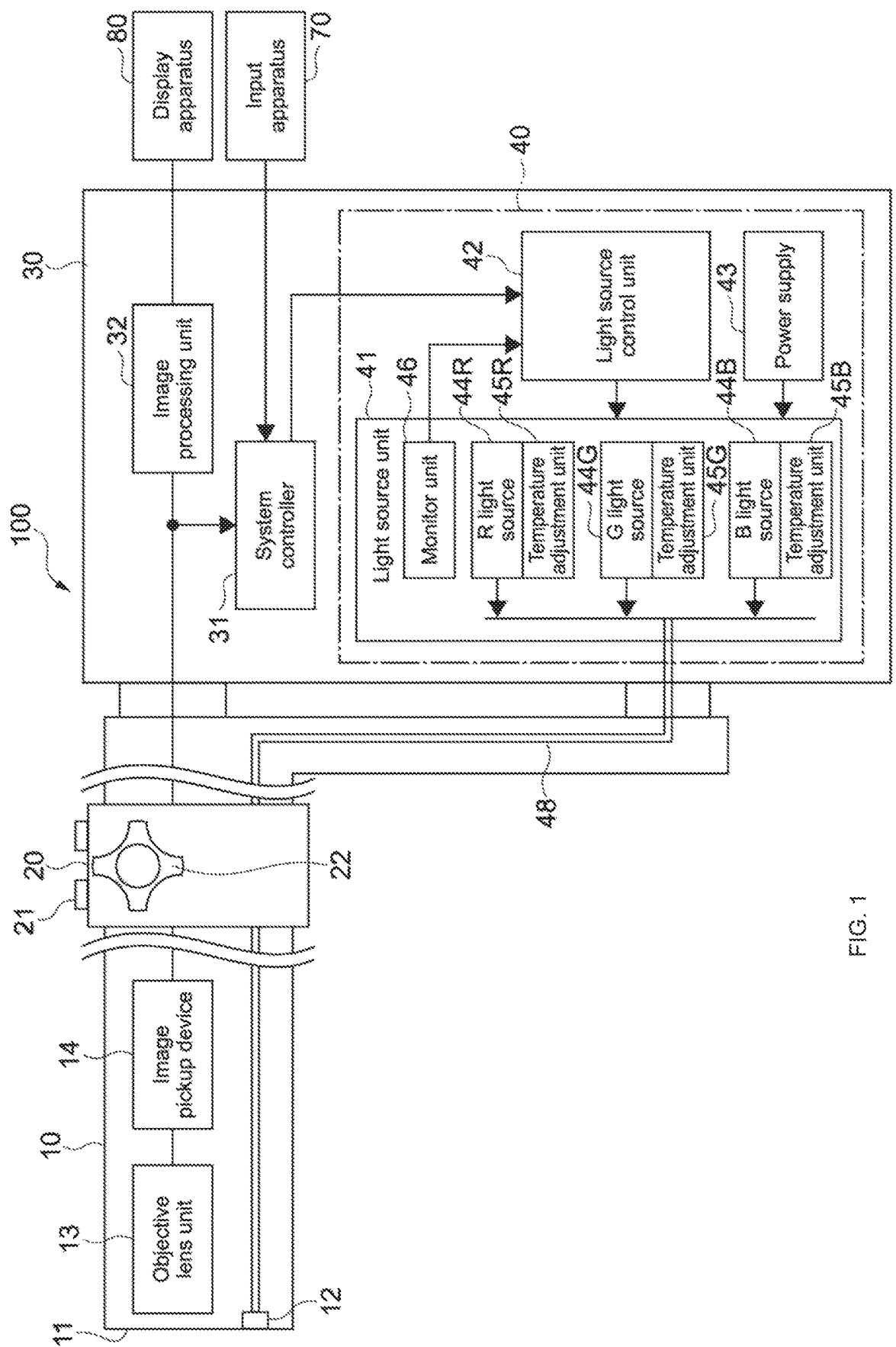
FIG. 1 A block diagram showing a configuration example of an endoscope apparatus according to an embodiment.

FIG. 1 is a block diagram showing a configuration example of an endoscope apparatus according to an embodiment of the present technology. An endoscope apparatus 100 includes an insertion unit 10, an operation unit 20, and a body unit 30.

The insertion unit 10 is a flexible part to be inserted into a paries. At a tip end portion 11 of the insertion unit 10, an irradiation port 12 for illumination light to be irradiated onto a to-be-observed area is provided. Also provided at the tip end portion 11 are an objective lens unit 13 and an image pickup device 14 for acquiring image information of the to-be-observed area. As the image pickup device 14, for example, a CMOS (Complementary Metal-Oxide Semiconductor) sensor, a CCD (Charge Coupled Device) sensor, or the like is used.

The operation unit 20 is connected to a base end of the insertion unit 10. Various switches 21, an angle knob 22, and the like are provided in the operation unit 20. For example, by operating the switch 21, air, water, or the like is supplied to the to-be-observed area via a supply port (not shown). Further, by operating the angle knob 22, a curvature mechanism provided at the tip end portion 11 is operated so that the tip end portion 11 is curved in an arbitrary direction at an arbitrary angle. A forceps port into which a treatment tool such as forceps and electrodes is inserted, and the like may be provided in the operation unit 20.

The body unit 30 includes a system controller 31, an image processing unit 32, and a light source apparatus 40 according to the present technology. The system controller 31 collectively controls the entire system of the endoscope apparatus 100. For example, the system controller 31 instructs the light source apparatus 40 to emit illumination light and, in synchronization with this, causes the image pickup device 14 to acquire image information of a to-be-observed area.

Further, as shown in FIG. 1, an input apparatus 70 is connected to the system controller 31 via an input/output interface (not shown). The input apparatus 70 is, for example, a device that is operated by an operator, such as a keyboard, a mouse, and a touch panel. The system controller 31 executes processing corresponding to an operation input via the input apparatus 70.

The system controller 31 includes, for example, a CPU, a RAM, a ROM, and the like and controls the entire system by the CPU loading a control program recorded in advance in the ROM in the RAM and executing it. The configuration of the system controller 31 is not limited, and arbitrary hardware and software may be used. For example, devices such as FPGA (Field Programmable Gate Array) and ASIC (Application Specific Integrated Circuit) may be used.

The image processing unit 32 executes various types of image processing such as color interpolation and gamma correction on image information output from the image pickup device 14. The image information processed by the image processing unit 32 is output to a display apparatus 80 connected to the body unit 30. The display apparatus 80 is a display device that uses, for example, liquid crystal, EL (Electro-Luminescence), or the like.

Light Source Apparatus

The light source apparatus 40 includes a light source unit 41, a light source control unit 42, and a power supply 43. The light source unit 41 includes a plurality of laser light sources (LDs) 44, a plurality of temperature adjustment units 45, and a monitor unit 46.

In this embodiment, a red laser light source 44R, a green laser light source 44G, and a blue laser light source 44B are arranged as the plurality of laser light sources 44. Laser light beams of the respective colors of RGB respectively emitted from the laser light sources 44 are synthesized by a synthetic optical system 47 (see FIG. 2) in the light source unit 41, for example. White light generated by the synthesis is emitted to a light guide (optical fiber) 48 connected to the light source unit 41 and is then guided to the illumination port 12 provided at the tip end portion 11 of the insertion unit 10 via the light guide 48.

Each of the red laser light source 44R, the green laser light source 44G, and the blue laser light source 44B corresponds to a light source portion in this embodiment. Therefore, the plurality of laser light sources 44 correspond to the plurality of light source portions. It should be noted that the number of light source portions is not limited.

The plurality of temperature adjustment units 45 are capable of respectively adjusting temperatures of the plurality of laser light sources 55. As shown in FIG. 1, in this embodiment, the plurality of temperature adjustment unit 45R is provided for the red laser light source 44R, and the temperature adjustment unit 45G is provided for the green laser light source 44G. Further, the temperature adjustment unit 45B is provided for the blue laser light source 44B. The temperature adjustment units 45 will be described later in detail.

It should be noted that the light source portion to be subjected to a temperature adjustment by the temperature adjustment unit 45 is not limited to a case where it is configured by a single laser light source 44 as in this embodiment. One light source portion may be configured by a plurality of laser light sources. Moreover, the present technology is also applicable to a case where the light source portion is configured by other solid-state light sources such as an LED, a xenon lamp, and the like. Furthermore, a plurality of temperature adjustment units 45 may be arranged with respect to a single light source portion.

The monitor unit 46 detects a current value and voltage value applied to each of the temperature adjustment units 45. The detected current value and voltage value of each of the temperature adjustment units 45 are output to the light source control unit 42. A method of detecting a current value and voltage value is not limited, and a well-known technology may be used, for example.

The light source control unit 42 controls start and stop of an operation of each of the laser light sources 44 and also controls the current value to be input to each of the laser light sources 44. The light source control unit 42 also controls a drive timing of each of the plurality of temperature adjustment units 45. The light source control unit 42 also detects power consumption of each of the temperature adjustment units 45 on the basis of the current value and voltage value output from the monitor unit 46. Power consumption is calculated from a product of the current value and voltage value.

For example, a microprocessor in which a CPU, a memory (RAM, ROM), I/O (Input/Output), and the like are mounted on 1 chip, or the like is used as the light source control unit 42. Devices such as FPGA, ASIC, and the like described above may also be used. In this embodiment, the light source control unit 42 functions as a drive control unit and a power detection unit.

The power supply 43 supplies power to the light source unit 41 via a power supply circuit (not shown). For example, power is consumed while the respective laser light sources 44 are driven or while the respective temperature adjustment units 45 are driven. In addition, the power supply 43 supplies power to the respective blocks of the light source apparatus 40 and the respective blocks of the endoscope apparatus 100. It is also possible for the power supply 43 to be arranged in a block different from the light source apparatus 40 in the endoscope apparatus 100 and supply power to the light source apparatus 40 from the power supply 43. It should be noted that in a case where there is no supply of power from outside, the block of the power supply 43 may substitutionally be considered as a battery.

Figure 2:
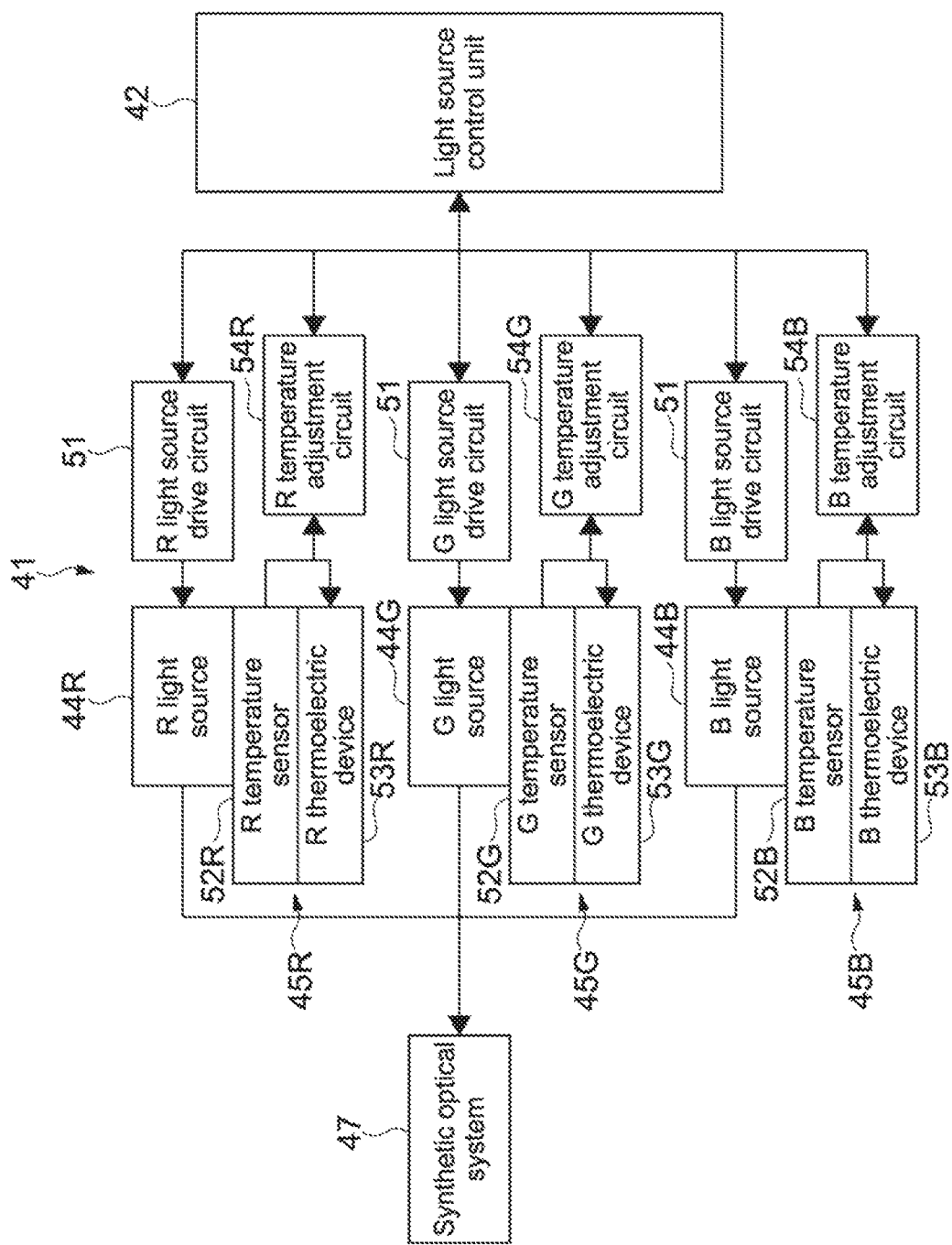
FIG. 2 A block diagram showing a configuration example of a light source unit shown in FIG. 1.

FIG. 2 is a block diagram showing a configuration example of the light source unit 41. It should be noted that an illustration of the monitor unit 46 is omitted. As shown in FIG. 2, the respective laser light sources 44 of RGB are connected to drive circuits 51. Current values are set by the light source control unit 42 and output to the drive circuits 51. The drive circuits 51 apply currents to the laser light sources 44 on the basis of the current values.

Each of the temperature adjustment units 45 includes a temperature sensor 52, a thermoelectric device 53, and a temperature adjustment circuit 54. The temperature sensors 52 each function as a temperature detection unit in this embodiment and detect respective temperatures of the plurality of laser light sources 44. The detected temperatures are output to the light source control unit 42. A thermistor, a thermocouple, or the like is used as the temperature sensor 52, for example.

The thermoelectric device 53 is a device capable of exchanging electric energy and thermal energy and cools or heats an object in accordance with an application of power. A Peltier device or the like is used as the thermoelectric device 53, for example. The temperature adjustment circuit 54 controls operations of the thermoelectric device 53. By the temperature adjustment circuit 54 being driven by the light source control unit 42, cooling or heating by the thermoelectric device 53 is performed. It should be noted that a specific configuration of the temperature adjustment circuit 54 is not limited. In this embodiment, the drive of the temperature adjustment circuit 54 corresponds to drive of the temperature adjustment unit 45.

Method of Driving Each Temperature Adjustment Circuit

The plurality of temperature adjustment circuits 54 are controlled for setting the respective laser light sources 44 at an optimal use temperature mainly at a preparation stage for driving the light source apparatus 40. Specifically, by driving the respective temperature adjustment circuits 54, the temperatures of the laser light sources 44 are respectively adjusted to target temperatures. Although a specific value of the target temperature is not limited, the target temperature is 25° C. in this embodiment. The method described below for driving the respective temperature adjustment circuits 54 corresponds to a temperature control method according to the present technology.

The light source control unit 42 executes PID control on the respective temperature adjustment circuits 54 on the basis of the temperatures fed back from the temperature sensors 52. Specifically, the PID control is executed using predetermined PID parameters while a target value is set at 25° C. Accordingly, temperature adjustments can be performed with high accuracy.

The light source control unit 42 is also capable of controlling drive timings of the respective temperature adjustment circuits 54 on the basis of the drive states of the respective temperature adjustment circuits 54. The drive timing is a drive start timing and is a PID control start timing in this embodiment.

Figure 3:
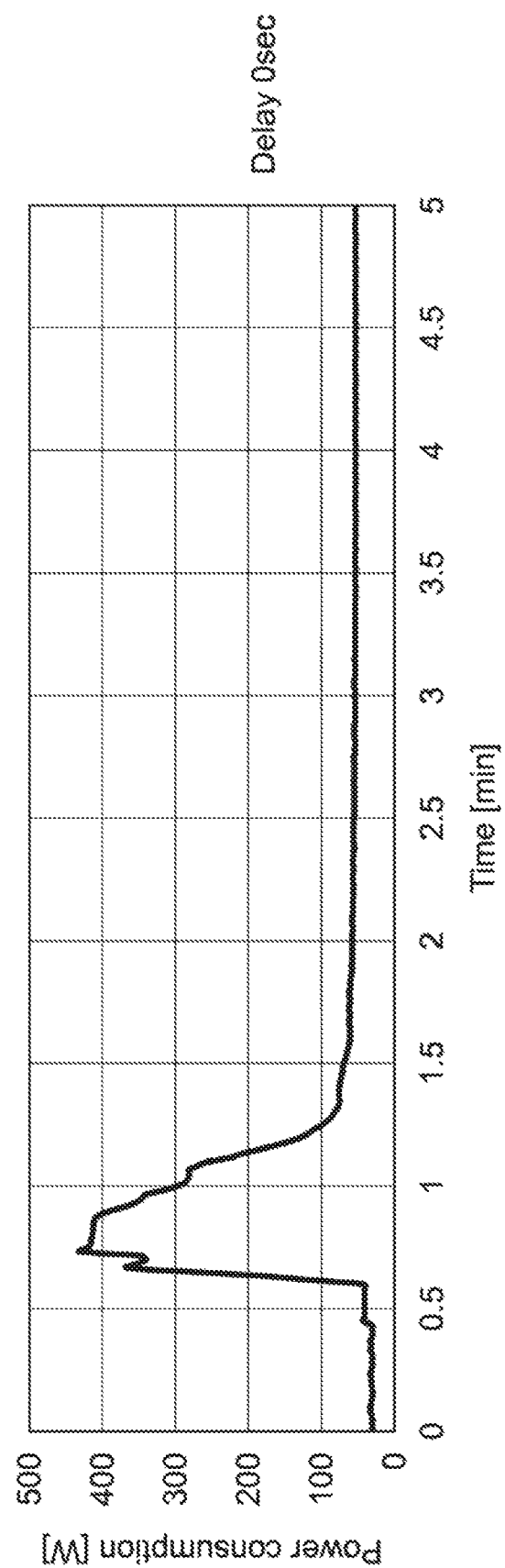
FIG. 3 A graph showing a transition of power consumption in a case where drive timings of temperature adjustment circuits are set to be equal to one another.
Figure 4:
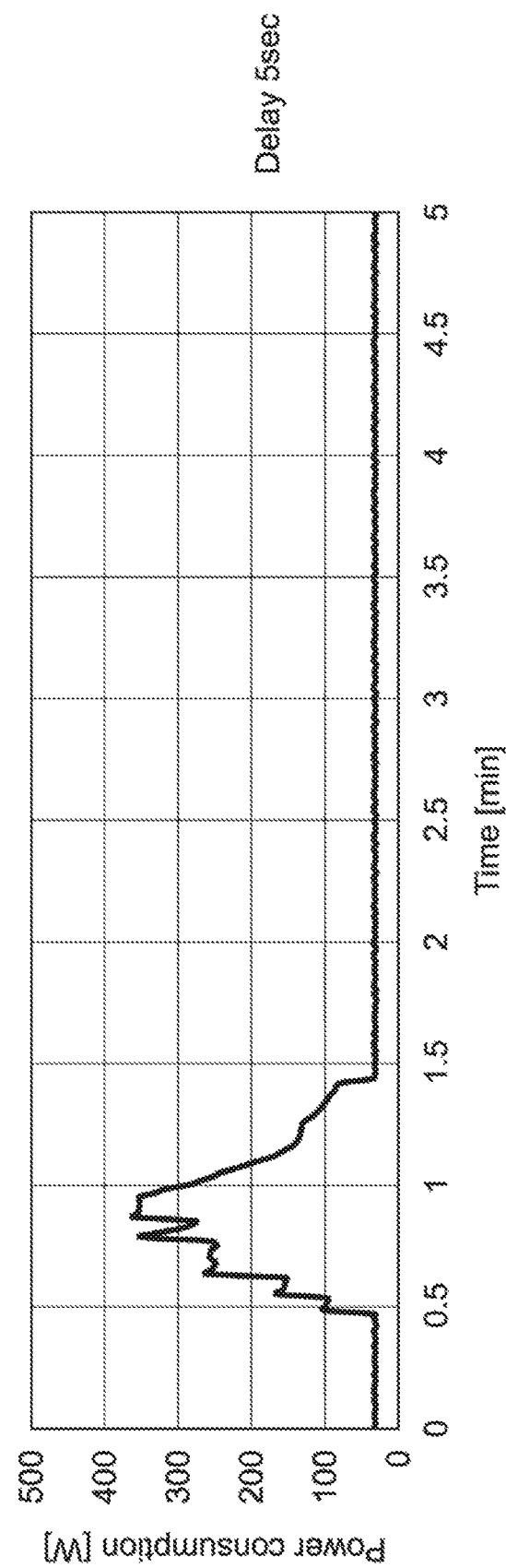
FIG. 4 A graph showing a transition of power consumption in a case where the drive timing is delayed 5 seconds.
Figure 5:
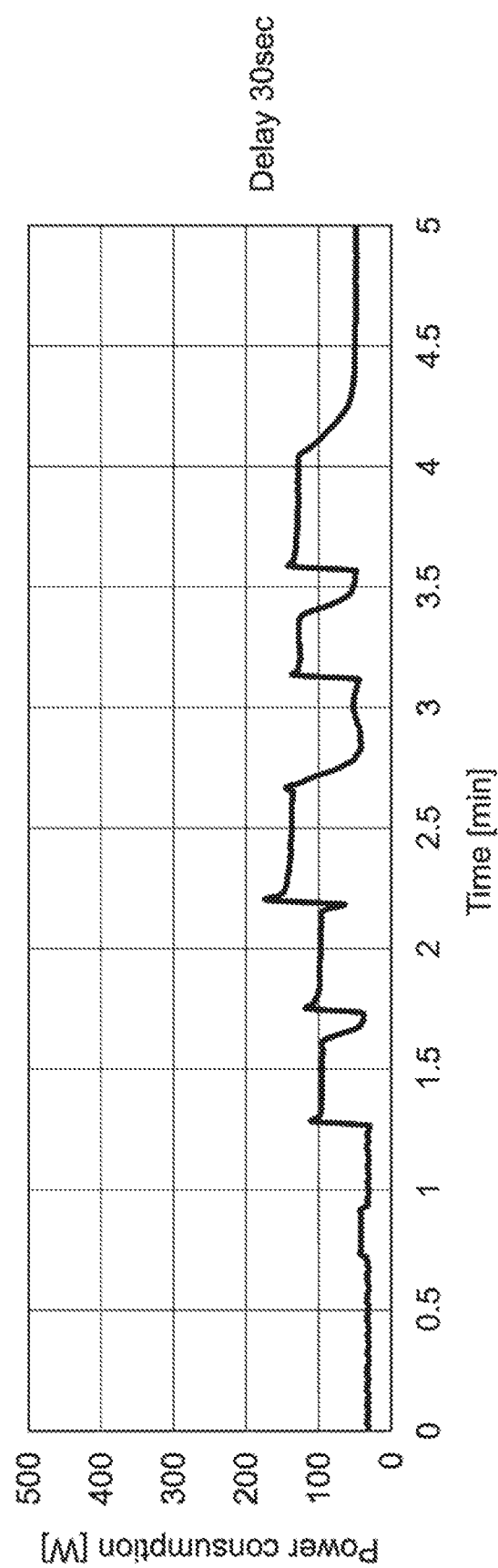
FIG. 5 A graph showing a transition of power consumption in a case where the drive timing is delayed 30 seconds.

FIGS. 3 to 5 are graphs showing transitions of power consumption during temperature adjustments of the respective laser light sources 44. These graphs are graphs in a case where the laser light sources 44 are adjusted to 25° C. from a state where an environmental temperature is 35° C.

FIG. 3 is a graph in a case where the drive timings of the temperature adjustment circuits 54 are set to be equal to one another, that is, the plurality of temperature adjustment circuits 54 are driven at the same time. Because the plurality of temperature adjustment circuits 54 cool the temperatures of the laser light sources 44 at the same time, power exceeding 400 W is consumed instantaneously. After that, each of the temperature adjustment circuits 54 is put to a stationary state, and power consumption is stabilized at 100 W or less.

It should be noted that the stationary state refers to a state where a fed-back temperature hardly changes and is typically a driving state for maintaining the laser light sources 44 at the target temperature of 25° C. Further, in the present disclosure, the expression "instantaneous power consumption" is used for comparing it with entire power consumption during an entire drive time. Typically, power consumption until the respective temperature adjustment circuits 54 are put to the stationary state corresponds to the instantaneous power consumption.

FIGS. 4 and 5 are graphs in a case where the drive timings of the temperature adjustment circuits 54 are delayed, that is, the plurality of temperature adjustment circuits 54 are sequentially driven at predetermined time intervals.

FIG. 4 is a graph in a case where a delay time (interval) is 5 seconds, and it can be seen that the instantaneous power consumption is reduced to a value of 400 W or less. FIG. 5 is a graph in a case where the delay time is 30 seconds, and it is possible to reach the target temperature with power consumption of 200 W or less.

Figure 6:
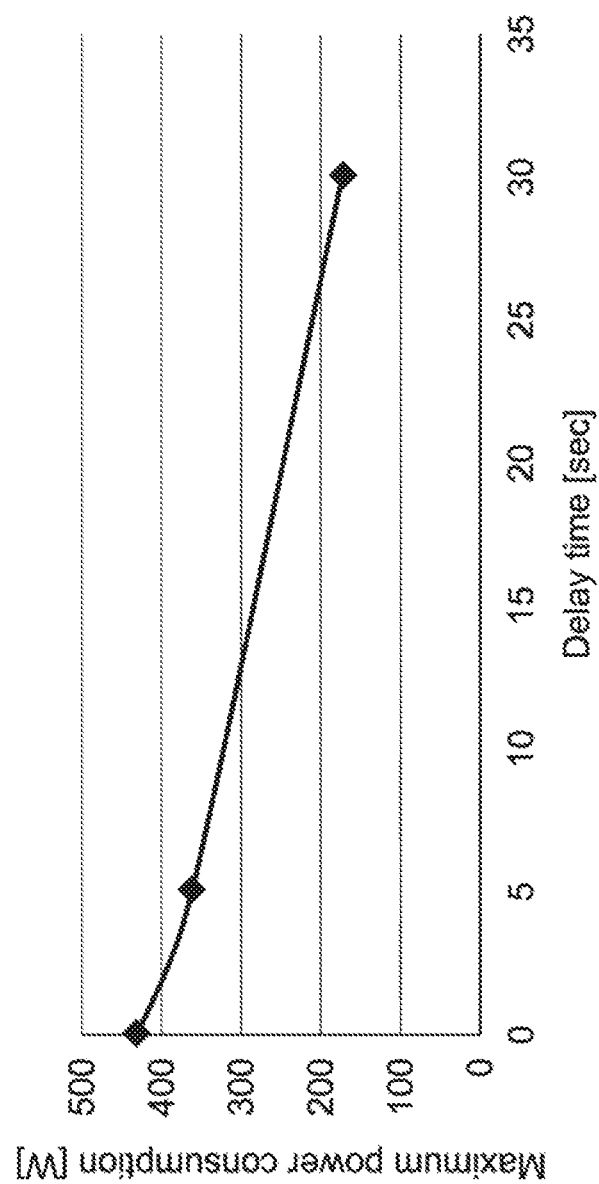
FIG. 6 A graph showing a relationship between a delay time and instantaneous maximum power consumption.

FIG. 6 is a graph showing a relationship between the delay time and instantaneous maximum power consumption. As shown in FIG. 6, it can be seen that a power consumption peak value becomes smaller as the delay time becomes larger. Specifically, by driving the plurality of temperature adjustment units 45 such that the respective drive timings differ from one another, the instantaneous maximum power consumption can be reduced.

In a case where the instantaneous maximum power consumption can be reduced, a power supply capacity requisite for driving the light source apparatus 40 can be reduced. Therefore, it becomes possible to miniaturize the power supply 43 of the light source apparatus 40 and realize miniaturization of the entire apparatus. Further, stable battery drive becomes possible during an emergency medical care in a situation where there is no supply of power from outside, for example. As a result, it becomes possible to realize a compact medical light source apparatus in which stable battery drive can be performed during an emergency medical care in a medical field and the like, an endoscope apparatus including this, and the like.

Further, since the instantaneous maximum power consumption can be reduced, an assumable leakage current can be sufficiently suppressed. In other words, safety regarding patients and the like can be additionally improved. Furthermore, since the temperatures of the laser light sources 44 can be adjusted to the target temperature, a lifetime of the laser light sources 44 can be prolonged, and a wavelength of emission light can be prevented from changing.

As shown in FIGS. 3 to 5, the maximum power consumption can be reduced by shifting the drive timings of the respective temperature adjustment circuits 54. Meanwhile, a total time required for all the laser light sources 44 to reach the target temperature becomes long. In other words, the maximum power consumption and the time required to reach the target temperature are in a tradeoff relationship. For example, the delay time is set in consideration of this relationship between the maximum power consumption and the time required to reach the target temperature. Of course, the present technology is not limited to this, and the delay time may be set arbitrarily.

For example, in a case where maximum power consumable in the temperature adjustments of the laser light sources 44 is determined in advance, the delay time is set such that the time required to reach the target temperature becomes as short as possible within a range where the maximum power consumption in the temperature adjustments becomes smaller than this maximum power. It should be noted that the maximum power consumable in the temperature adjustments is determined on the basis of the capacity of the power supply 43, the drive state of the other blocks in the light source apparatus 40, such as the laser light sources 44, and the like, for example. Moreover, the maximum power may also be determined while depending on the drive state of other blocks in the endoscope apparatus 100.

It is also possible to set the delay time on the basis of a difference between the maximum power and a sum of power consumption of the respective temperature adjustment circuits 54 (hereinafter, simply referred to as margin). Specifically, the delay time is set such that the margin falls within a predetermined range, typically such that the margin becomes sufficiently small. Accordingly, the time required to reach can be sufficiently shortened within an allowable power consumption range.

In the case where the delay time is 30 seconds as shown in FIG. 5, there exists a part where power consumption is temporarily lowered and rises again before all the temperature adjustment circuits 54 are put to the stationary state. In the sequentially-driven temperature adjustment circuits 54, this part corresponds to a time slot where the next temperature adjustment circuit 54 is driven after the temperature adjustment circuit 54 that has been driven first is put to the stationary state and power consumption is thus lowered. For example, by setting the delay time such that such a time slot is not generated, it becomes possible to shorten the time required to reach while suppressing an increase of the maximum power consumption.

By sequentially driving the plurality of drive circuits 54 at certain time intervals, the instantaneous maximum power consumption can be reduced by simple processing. On the other hand, in many cases, an amount of heat generated from the laser light sources 44, a specification of the Peltier device, and the like differ for each light source apparatus 40, and the instantaneous maximum power consumption and the time required to reach the target temperature do not become constant. Therefore, it is effective to control each of the drive timings in accordance with the drive state of each of the temperature adjustment circuits 54.

For example, the light source control unit 42 controls the respective drive timings on the basis of the temperatures of the respective laser light sources 44 detected by the temperature sensors 52. For example, in a case where the temperature of the laser light source 44 is judged to have converged near the target temperature by the temperature adjustment circuit 54 that has been driven first, the next temperature adjustment circuit 54 is driven.

Referring back to FIG. 2, for example, the temperature adjustment circuit 54R (first temperature adjustment unit) that adjusts a temperature of the red laser light source 44R (first light source portion) is driven first, and in a case where the temperature of the red laser light source 44R detected by the temperature sensor 52R falls within a predetermined range, the temperature adjustment circuit 54G (second temperature adjustment unit) that adjusts a temperature of the green laser light source 44G (second light source portion) different from the red laser light source 44R is driven. Accordingly, the time required to reach the target temperature can be sufficiently shortened while reducing the instantaneous power consumption.

The predetermined range described above is a range within a target temperature ±n ° C., for example, and 0.5° C., 1° C., 1.5° C., or the like is used as the value of n, for example. Of course, the value is not limited to this, and the predetermined range may be set arbitrarily. Further, the predetermined range described above may be set as appropriate on the basis of the margin up to the maximum power consumable in temperature adjustments, the time required to reach the target temperature, and the like. It should be noted that the order of cooling the RGB laser light sources 44 is not limited.

Each of the drive timings may be controlled on the basis of the power consumption of the respective temperature adjustment circuits 54 calculated by the light source control unit 42. For example, in a case where the power consumption of the temperature adjustment circuit 54 that has been driven first is judged to have been reduced, the next temperature adjustment circuit 54 is driven.

For example, in a case where the temperature adjustment circuit 54R (first temperature adjustment unit) shown in FIG. 2 is driven and power consumption of the temperature adjustment circuit 54R becomes smaller than a predetermined threshold value, the temperature adjustment circuit 54G (second temperature adjustment unit) different from the temperature adjustment circuit 54R is driven. Accordingly, temperature adjustments can be executed efficiently with low power consumption, and the time required to reach the target temperature can be shortened.

The predetermined threshold value is not limited and only needs to be set as appropriate on the basis of the margin with respect to the maximum power consumable in temperature adjustments, the time required to reach the target temperature, and the like, for example. It should be noted that the order of driving the temperature adjustment circuits 54 is not limited, and a priority order may be set as follows, for example.

FIGS. 7A and 7B are diagrams for explaining an example of setting the priority order for driving the temperature adjustment circuits 54 and are graphs schematically showing transitions of power consumption in the temperature adjustment. For example, the priority order is set on the basis of the power consumption of the temperature adjustment circuits 54 that have adjusted the temperatures of the laser light sources 44 and have been put to the stationary state. In other words, the temperature adjustment circuit 54 that has low power consumption in the stationary state is driven preferentially.

As shown in FIGS. 7A and 7B, it is assumed that maximum power consumable is 300 W, for example. In addition, it is assumed that, regarding the respective temperature adjustment circuits 54, power consumption P1 requisite for the respective laser light sources 44 to reach the target temperature and power consumption P2 in the stationary state are set to the following values.
Temperature adjustment circuit 54R
Power consumption P1: 100 W
Power consumption P2: 25 W
Temperature adjustment circuit 54G
Power consumption P1: 150 W
Power consumption P2: 50 W
Temperature adjustment circuit 54B
Power consumption P1: 200 W
Power consumption P2: 75 W As shown in FIG. 7A, in a case of driving from the temperature adjustment circuit 54 having largest power consumption P2 in the stationary state, the temperature adjustment circuit 54B is driven first and put to the stationary state at a time t1. At this time, the remaining consumable power becomes 225 W, so the temperature adjustment circuit 54R is driven after the temperature adjustment circuit 54G is driven and put to the stationary state at a time t2. Then, the three laser light sources 54 reach the target temperature at a time t3 where the temperature adjustment circuit R is put to the stationary state.

As shown in FIG. 7B, in a case of preferentially driving from that having smallest power consumption P2 in the stationary state, the temperature adjustment circuit 54R is driven first. At that time, since there is marginal 200 W as the power consumption, the temperature adjustment circuit 54G can be driven at the same time. After the temperature adjustment circuits 54R and 54G are put to the stationary state at a time t4, the temperature adjustment circuit 54B is driven and put to the stationary state at a time t5. As a result, the time required for the three laser light sources 44 to reach the target temperature can be significantly reduced.

By preferentially driving that having lower power consumption P2 in the stationary state in this way, the possibility of the plurality of temperature adjustment circuits 54 becoming capable of being driven at the same time becomes high, and the time required to reach the target temperature can be shortened. This technology is also applicable to a case where the temperature adjustment circuits 54 are driven at predetermined time intervals and a case where the drive timings are controlled on the basis of the temperatures of the respective laser light sources 44 and the power consumption of the respective temperature adjustment circuits 54. In other words, in a case where a single temperature adjustment circuit 54 is driven, other temperature adjustment circuits may also be driven simultaneous with that temperature adjustment circuit 54 if there is room for power consumption.

It should be noted that a magnitude relationship of the power consumption P2 in the stationary state is established in a level that can be said to be substantially synonymous with a magnitude relationship of the power consumption P1 for the respective laser light sources 44 to reach the target temperature. Focusing on this point, the drive priority level is set on the basis of the power consumption P2 in the stationary state. Of course, focusing on the power consumption P1 for the respective laser light sources 44 to reach the target temperature, it is also possible to preferentially start the drive from that having lower power consumption P1.

The priority order based on the power consumption P2 and the power consumption P1 may be set by an operator or may be set automatically by the light source control unit 42 on the basis of the calculated power consumption of each of the temperature adjustment circuits 54.

Figure 8A:
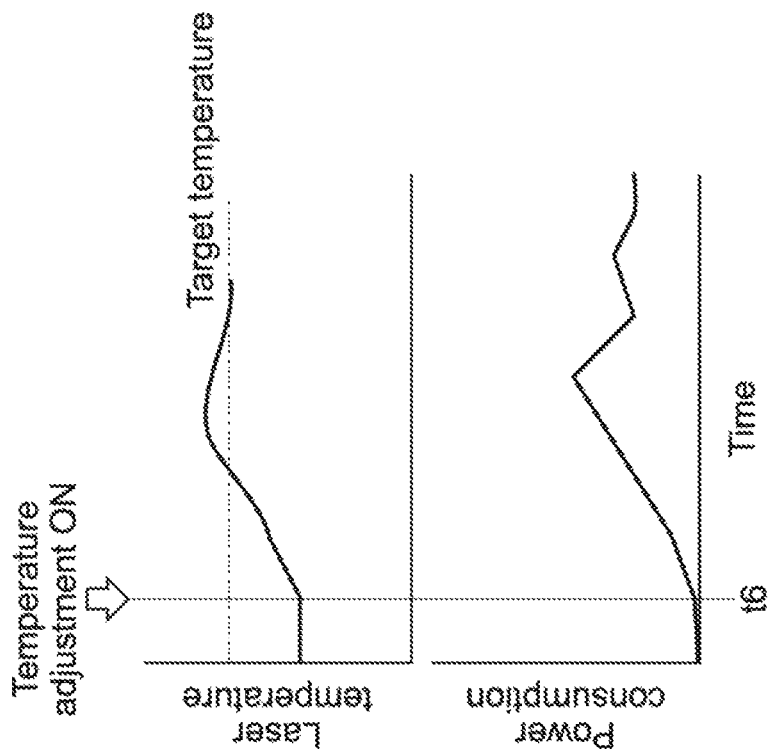
FIGS. 8A and 8B Schematic graphs for explaining a drive method for adjusting PID parameters.
Figure 8B:
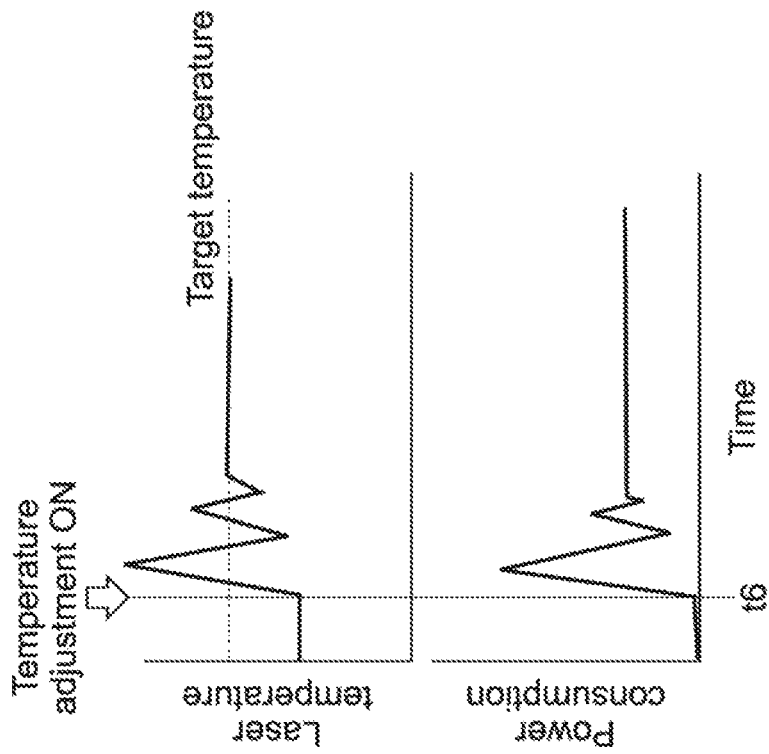

FIGS. 8A and 8B are schematic graphs for explaining a drive method for adjusting PID parameters. It should be noted that herein, descriptions will be given while taking a case where the current temperature is lower than the target temperature as an example. The present technology is also similarly applicable to a case where the current temperature is to be lowered toward the target temperature and a case where the current temperature is to be raised toward the target temperature.

The drive method shown in FIGS. 8A and 8B is controlled such that the respective drive timings of the plurality of temperature adjustment circuits 54 become equal to one another (t6). Meanwhile, regarding PID parameters used for the PID control on each of the plurality of temperature adjustment circuits 54, different PID parameters are set for the respective temperature adjustment circuits 54.

For example, as shown in FIG. 8A, a PID parameter that sets the current temperature to approach the target temperature is set in a certain temperature adjustment circuit 54. In this case, a power consumption peak becomes almost the same timing as the drive start. On the other hand, as shown in FIG. 8B, a PID parameter that sets the current temperature to gradually approach the target temperature is set in another temperature adjustment circuit 54. In this case, the power consumption reaches its peak at a timing a while after the drive start.

By setting the PID parameters of the respective temperature adjustment circuits 54 to differ from one another in this way, it becomes possible to shift the power consumption peaks of the respective temperature adjustment circuits 54. As a result, it becomes possible to dull the peak of the instantaneous power consumption before the respective temperature adjustment circuits 54 are put to the stationary state. The PID parameters to be set in the respective temperature adjustment circuits 54 are set as appropriate on the basis of, for example, the margin up to the maximum power consumable in temperature adjustments, the time required to reach the target temperature, and the like.

It should be noted that in the case of executing the other drive methods described above, the PID parameters may be set on the basis of the margin and the like. For example, in a case where the margin is large, the time required to reach the target temperature is shortened while allowing an increase of the power consumption by raising a gain of the PID parameters. In a case where the margin is small, power consumption is suppressed while allowing an increase of the time required to reach by lowering the gain of the PID parameters. Such control may be executed dynamically, for example.

Figure 9:
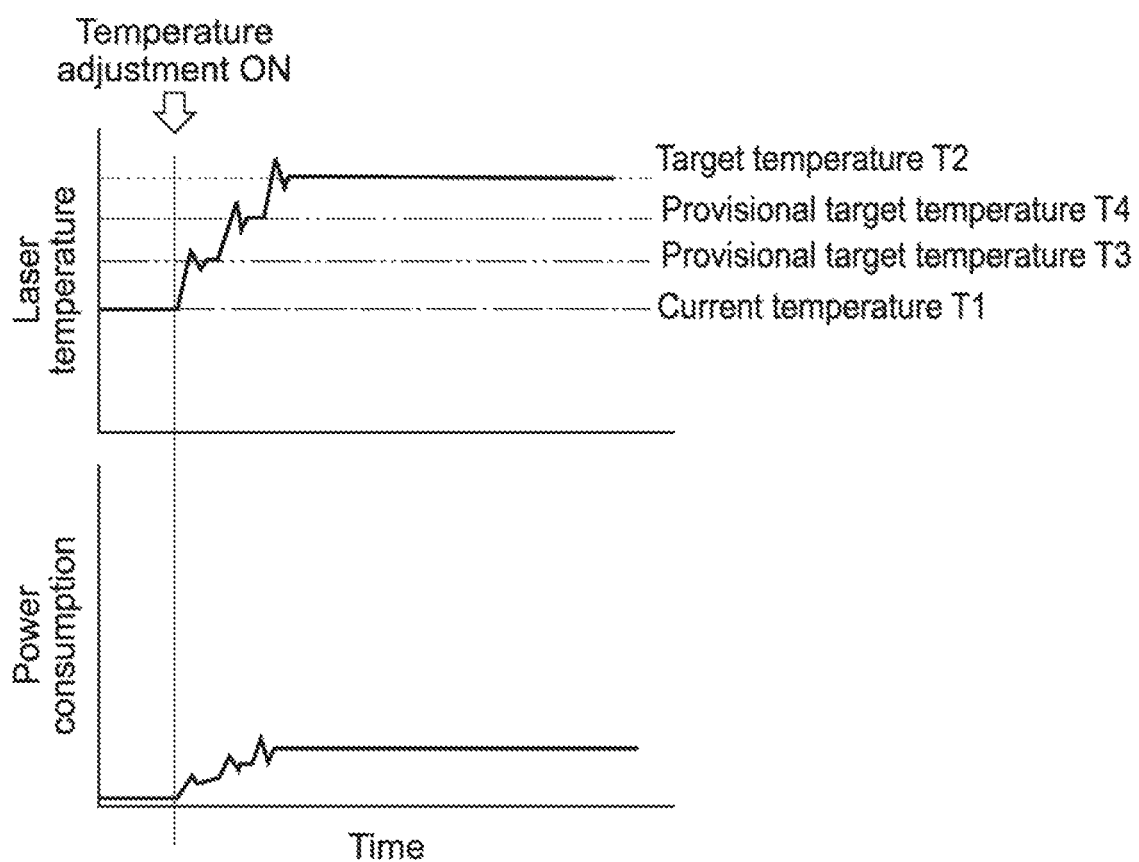
FIG. 9 A schematic graph for explaining a method of adjusting a target value in PID control.

FIG. 9 is a schematic graph for explaining a method of adjusting a target value in the PID control. As shown in FIG. 9, provisional target temperatures T3 and T4 may be set within a range between a current temperature T1 of the respective laser light sources 44 and a final target temperature T2. In addition, the PID control that sets the provisional target temperatures T3 and T4 and the target temperature T2 as the target values may be executed stepwise.

Specifically, the PID control that sets the provisional target temperature T3 closest to the current temperature T1 as the target value is executed, and the PID control that sets the provisional target temperature T4 next closest to the current temperature T1 as the target value is executed after that. Finally, the PID control that sets the target temperature T2 as the target value is executed.

In executing the PID control, the power consumption of the temperature adjustment circuits 54 becomes larger as a difference between the current temperature T1 and the temperature to be a target value becomes larger. Therefore, as shown in FIG. 9, by setting the provisional target temperatures T3 and T4 and restricting the temperature difference in the PID control, power consumption can be reduced without changing the PID parameters, for example.

It should be noted that the number of provisional target temperatures is not limited, and one or more provisional target temperatures may be set as appropriate. Provisional target temperatures that differ from one another may be set with respect to the respective temperature adjustment circuits 54. The method of setting the provisional target temperatures is not limited, and one or more provisional target temperatures are set such that the current temperature T1 and the target temperature T2 are equally divided, for example. Alternatively, the provisional target temperatures may be set finely in a temperature range close to the current temperature T1 and set with intervals in a temperature range close to the target temperature T2. An opposite setting is also possible.

Other Embodiments

The present technology is not limited to the embodiment described above, and various other embodiments can be realized.

In the descriptions above, the case of using the laser light sources of three colors of RGB has been described. The present technology is not limited to this, and a laser light source for excitation light for exciting a fluorescent pigment injected into a human body may be arranged, for example. For example, the RGB laser light sources, an infrared laser light source that emits special light such as excitation light, and the like are arranged, and an image obtained by white light and an image obtained by special light are photographed alternately. The present technology is also applicable to such a configuration.

The setting of the provisional target temperatures shown in FIG. 9 is also applicable to a case where only a single temperature adjustment circuit is used, and it is possible to reduce the instantaneous power consumption before being put to the stationary state.

It should be noted that the present technology is applicable to not only the endoscope apparatus but also other apparatuses and systems in medical and biological fields, such as a light microscope. In addition, the light source apparatus and temperature control method according to the present technology may also be applied to apparatuses and systems of various fields, such as an optical recording system and a semiconductor exposure apparatus. Moreover, the temperature adjustment target is not limited to the light source, and the present technology is also applicable to a case of adjusting temperatures of other devices and the like, an example thereof being crystal temperature control or the like.

At least two of the feature portions according to the present technology described above can be combined. In other words, various feature portions described in the respective embodiments may be arbitrarily combined without distinguishing the embodiments from one another. Moreover, the various effects described above are mere examples and should not be limited thereto, and other effects may also be exerted.

It should be noted that the present technology can also take the following configurations.

(1) A light source apparatus, including:
  a plurality of light source portions;
  a plurality of temperature adjustment units capable of respectively adjusting temperatures of the plurality of light source portions; and
  a drive control unit capable of controlling a drive timing of each of the plurality of temperature adjustment units.

(2) The light source apparatus according to (1), in which the drive control unit drives the plurality of temperature adjustment units such that the respective drive timings differ from one another.

(3) The light source apparatus according to (1) or (2), in which
  the drive control unit sequentially drives the plurality of temperature adjustment units at predetermined time intervals.

(4) The light source apparatus according to any one of (1) to (3), further including
  a temperature detection unit capable of detecting a temperature of each of the plurality of light source portions,
  in which the drive control unit controls each of the drive timings on the basis of the temperature detected by the temperature detection unit.

(5) The light source apparatus according to (4), in which the drive control unit drives a first temperature adjustment unit that adjusts a temperature of a first light source portion and drives, in a case where the temperature of the first light source portion falls within a predetermined range, a second temperature adjustment unit that adjusts a temperature of a second light source portion different from the first light source portion.

(6) The light source apparatus according to any one of (1) to (5), further including
  a power detection unit capable of detecting power consumption of each of the plurality of temperature adjustment units,
  in which the drive control unit controls each of the drive timings on the basis of the power consumption detected by the power detection unit.

(7) The light source apparatus according to (6), in which the drive control unit drives a first temperature adjustment unit and drives, in a case where power consumption of the first temperature adjustment unit becomes smaller than a predetermined threshold value, a second temperature adjustment unit different from the first temperature adjustment unit.

(8) The light source apparatus according to any one of (1) to (7), in which
  the drive control unit preferentially drives the temperature adjustment unit having lower expense power out of the temperature adjustment units that have adjusted the temperatures of the light source portions and been put to a stationary state.

(9) The light source apparatus according to any one of (1) to (8), further including
  a temperature detection unit capable of detecting a temperature of each of the plurality of light source portions,
  in which the drive control unit is capable of PID (Proportional Integral Derivative)-controlling each of the plurality of temperature adjustment units on the basis of the temperature detected by the temperature detection unit.

(10) The light source apparatus according to (9), in which the drive control unit controls the respective drive timings such that the drive timings become equal to one another and sets PID parameters to be used for the PID control of each of the plurality of temperature adjustment units such that the PID parameters differ from one another.

(11) The light source apparatus according to (9) or (10), in which
  the drive control unit sets one or more provisional target temperatures within a range between a current temperature of the light source portion and a target temperature and executes stepwise the PID control that sets each of the one or more provisional target temperatures and the target temperature as a target value.

(12) The light source apparatus according to any one of (1) to (11), in which
  the drive control unit controls each of the drive timings on the basis of maximum power consumable in adjusting the temperature of each of the plurality of light source portions.

(13) The light source apparatus according to (12), further including
  a power detection unit capable of detecting power consumption of each of the plurality of light source portions,
  in which the drive control unit controls each of the drive timings such that a difference between the maximum power and a sum of power consumption detected by the power detection unit falls within a predetermined range.

REFERENCE SIGNS LIST

T1 current temperature
T2 target temperature
T3, T4 provisional target temperature
40 light source apparatus
41 light source unit
42 light source control unit
44 plurality of laser light sources
45 temperature adjustment unit
46 monitor unit
52 temperature sensor
53 electric device
54 temperature adjustment circuit
100 endoscope apparatus

The invention claimed is:

1. A system for controlling temperatures of a plurality of light source portions, the system comprising:
  the plurality of light source portions;
  a plurality of temperature adjustment units configured to adjust the temperatures of the plurality of light source portions; and a drive control unit configured to:
  adjust a temperature of a first light source portion of the plurality of light source portions; and
  adjust a temperature of a second light source portion of the plurality of light source portions based on the temperature of the first light source portion that is within a threshold range, wherein the second light source portion is different from the first light source portion.

2. The system according to claim 1, wherein the drive control unit is further configured to control a drive timing of each temperature adjustment unit of the plurality of temperature adjustment units such that the drive timing of each temperature adjustment unit of the plurality of temperature adjustment units is different.

3. The system according to claim 2, wherein the drive control unit is further configured to sequentially drive the plurality of temperature adjustment units at specific time intervals.

4. The system according to claim 1, wherein the drive control unit is further configured to drive a temperature adjustment unit that has a lowest expense power out of the plurality of temperature adjustment units that have adjusted the temperatures of the plurality of light source portions and that are in a stationary state.

5. The system according to claim 1, wherein a light irradiated from the plurality of light source portions passes through one of an endoscope or a microscope and irradiates onto a body tissue.

6. A system for controlling temperatures of a plurality of light source portions, the system comprising:
  the plurality of light source portions;
  a plurality of temperature adjustment units configured to adjust the temperatures of the plurality of light source portions;
  a temperature detection unit configured to detect a temperature of each light source portion of the plurality of light source portions; and
  a drive control unit configured to:
    control, by a Proportional Integral Derivative (PID) process, each temperature adjustment unit of the plurality of temperature adjustment units based on the temperature detected by the temperature detection unit;
    control a drive timing of each temperature adjustment unit of the plurality of temperature adjustment units such that the drive timing of each temperature adjustment unit of the plurality of temperature adjustment units is equal; and
    set a PID parameter corresponding to the PID process of each temperature adjustment unit of the plurality of temperature adjustment units such that the PID parameter of each temperature adjustment unit of the plurality of temperature adjustment units is different.

7. The system according to claim 6, wherein the drive control unit is further configured to:
  drive a first temperature adjustment unit of the plurality of temperature adjustment units, wherein the first temperature adjustment unit is configured to adjust a temperature of a first light source portion of the plurality of light source portions; and
  drive a second temperature adjustment unit of the plurality of temperature adjustment units based on the temperature of the first light source portion that is within a threshold range, wherein
  the second temperature adjustment unit is configured to adjust a temperature of a second light source portion of the plurality of light source portions, and
  the second light source portion is different from the first light source portion.

8. The system according to claim 6, wherein a light irradiated from the plurality of light source portions passes through one of an endoscope or a microscope and irradiates onto a body tissue.

9. A system for controlling temperatures of a plurality of light source portions, the system comprising:
  the plurality of light source portions;
  a plurality of temperature adjustment units configured to adjust the temperatures of the plurality of light source portions;
  a temperature detection unit configured to detect a temperature of each light source portion of the plurality of light source portions; and
  a drive control unit configured to:
    control, by a Proportional Integral Derivative (PID) process, each temperature adjustment unit of the plurality of temperature adjustment units based on the temperature detected by the temperature detection unit;
    set at least one provisional target temperature within a range between a current temperature of the plurality of light source portions and a target temperature of the plurality of light source portions; and
    execute stepwise the PID process that sets each of the at least one provisional target temperature and the target temperature as a target value.

10. The system according to claim 9, wherein the drive control unit is further configured to:
  drive a first temperature adjustment unit of the plurality of temperature adjustment units, wherein the first temperature adjustment unit is configured to adjust a temperature of a first light source portion of the plurality of light source portions; and
  drive a second temperature adjustment unit of the plurality of temperature adjustment units based on the temperature of the first light source portion that is within a threshold range, wherein
  the second temperature adjustment unit is configured to adjust a temperature of a second light source portion of the plurality of light source portions, and
  the second light source portion is different from the first light source portion.

11. A method for controlling temperatures of a plurality of light source portions, the method comprising:
  detecting a temperature of each temperature adjustment unit of a plurality of temperature adjustment units configured to adjust the temperatures of the plurality of light source portions;
  controlling, by a Proportional Integral Derivative (PID) process, each temperature adjustment unit of the plurality of temperature adjustment units based on the detected temperature of each temperature adjustment unit of the plurality of temperature adjustment units;
  controlling a drive timing of each temperature adjustment unit of the plurality of temperature adjustment units such that the drive timing of each temperature adjustment unit of the plurality of temperature adjustment units is equal; and
  settling a PID parameter corresponding to the PID process of each temperature adjustment unit of the plurality of temperature adjustment units such that the PID parameter of each temperature adjustment unit of the plurality of temperature adjustment units is different.

12. A method for controlling temperatures of a plurality of light source portions, the method comprising:
adjusting the temperatures of the plurality of light source portions;
adjusting a temperature of a first light source portion of the plurality of light source portions; and
adjusting a temperature of a second light source portion of the plurality of light source portions based on the temperature of the first light source portion that is within a threshold range, wherein the second light source portion is different from the first light source portion.

13. A method for controlling temperatures of a plurality of light source portions, the method comprising:
detecting a temperature of each temperature adjustment unit of a plurality of temperature adjustment units configured to adjust the temperatures of the plurality of light source portions;
controlling, by a Proportional Integral Derivative (PID) process, each temperature adjustment unit of the plurality of temperature adjustment units based on the detected temperature of each temperature adjustment unit of the plurality of temperature adjustment units;
setting at least one provisional target temperature within a range between a current temperature of the plurality of light source portions and a target temperature of the plurality of light source portions; and
executing stepwise the PID process that sets each of the at least one provisional target temperature and the target temperature as a target value.

* * * * *